United States Patent
Mahieu et al.

(10) Patent No.: US 10,356,979 B2
(45) Date of Patent: Jul. 23, 2019

(54) MONITORING SYSTEM FOR AN AGRICULTURAL HARVESTER AND AGRICULTURAL HARVESTER

(71) Applicant: CNH Industrial America LLC, New Holland, PA (US)

(72) Inventors: Thomas Mahieu, Ypres (BE); Bart M. A. Missotten, Herent (BE)

(73) Assignee: CNH Industrial America LLC, New Holland, PA (US)

( * ) Notice: Subject to any disclaimer, the term of this patent is extended or adjusted under 35 U.S.C. 154(b) by 83 days.

(21) Appl. No.: 15/247,462

(22) Filed: Aug. 25, 2016

(65) Prior Publication Data

US 2017/0055444 A1    Mar. 2, 2017

(30) Foreign Application Priority Data

Aug. 25, 2015  (BE) .................................... 2015/5531

(51) Int. Cl.
| | |
|---|---|
| *A01D 41/12* | (2006.01) |
| *A01F 12/58* | (2006.01) |
| *A01D 41/127* | (2006.01) |
| *A01F 7/06* | (2006.01) |
| *A01F 12/28* | (2006.01) |
| *A01F 12/44* | (2006.01) |
| *A01F 12/46* | (2006.01) |
| *G01N 9/36* | (2006.01) |

(52) U.S. Cl.
CPC ....... *A01D 41/1243* (2013.01); *A01D 41/127* (2013.01); *A01D 41/1271* (2013.01); *A01F 7/06* (2013.01); *A01F 12/28* (2013.01); *A01F 12/446* (2013.01); *A01F 12/46* (2013.01); *A01F 12/58* (2013.01); *G01N 9/36* (2013.01)

(58) Field of Classification Search
CPC .............. A01D 41/127; A01D 41/1271; A01D 41/1243
See application file for complete search history.

(56) References Cited

U.S. PATENT DOCUMENTS

| | | | |
|---|---|---|---|
| 5,800,262 A | 9/1998 | Andersen et al. | |
| 5,837,906 A | 11/1998 | Palmer | |
| 6,059,656 A | * 5/2000 | Satzler | ................... A01F 12/56 460/116 |

(Continued)

FOREIGN PATENT DOCUMENTS

| | | |
|---|---|---|
| AT | 501307 A2 | 8/2006 |
| CZ | 20054 U1 | 9/2009 |

(Continued)

*Primary Examiner* — Alicia Torres
(74) *Attorney, Agent, or Firm* — Peter K. Zacharias; Patrick M. Sheldrake

(57) ABSTRACT

A monitoring system for a combine harvester. The monitoring system includes a sensor configured to provide a measurement wave to a flow of crop residue on the harvester and to receive a response wave from the flow of crop residue. The monitoring system further includes a processor having an input terminal for receiving a response signal of the sensor representative of the response wave. The processor is configured to determine a crop parameter associated with the density of the flow of crop based on the response signal of the sensor. The processor further has an output terminal for outputting a density signal representing the crop parameter.

11 Claims, 4 Drawing Sheets

(56) References Cited

U.S. PATENT DOCUMENTS

| | | |
|---|---|---|
| 7,367,880 B2 | 5/2008 | Hoskinson et al. |
| 8,627,766 B2 | 1/2014 | Verhaeghe et al. |
| 8,843,283 B2 | 9/2014 | Strelioff et al. |
| 9,668,418 B2 * | 6/2017 | Patton ................. A01D 41/1243 |
| 2005/0101363 A1 * | 5/2005 | Farley ................. A01D 41/1243 |
| | | 460/112 |
| 2011/0023439 A1 * | 2/2011 | Kendrick ........... A01D 41/1243 |
| | | 56/341 |
| 2014/0066146 A1 * | 3/2014 | Dilts .................. A01D 41/1243 |
| | | 460/111 |
| 2014/0171160 A1 * | 6/2014 | Ricketts ............. A01D 41/1243 |
| | | 460/1 |
| 2015/0046043 A1 | 2/2015 | Bollin et al. |
| 2015/0264864 A1 | 9/2015 | Branch et al. |
| 2016/0044869 A1 * | 2/2016 | Mayerle .................. A01F 12/40 |
| | | 460/1 |
| 2017/0086373 A1 * | 3/2017 | Mahieu ............. A01D 41/1243 |

FOREIGN PATENT DOCUMENTS

| | | | |
|---|---|---|---|
| CZ | 20218 U1 | 11/2009 | |
| DE | 4200770 A1 * | 7/1993 | ............... A24B 3/18 |
| DE | 102005050751 A1 | 8/2007 | |
| EP | 1813142 A1 | 8/2007 | |
| EP | 2272312 A1 | 1/2011 | |
| FI | 80564 B | 3/1990 | |
| JP | 2777010 B2 | 7/1998 | |
| JP | H10313660 A | 12/1998 | |

\* cited by examiner

MONITORING SYSTEM FOR AN AGRICULTURAL HARVESTER AND AGRICULTURAL HARVESTER

FIELD OF THE INVENTION

The invention relates to the field of agricultural harvesters such as combines which including a threshing assembly for separating the various components of a harvested crop, e.g. grain and straw.

In particular, the invention relates to a monitoring system for assessing the quality of straw.

BACKGROUND OF THE INVENTION

An agricultural harvester, also referred to as a combine or combine harvester because it typically combines multiple harvesting functions, typically includes a header for removing a crop from a field and a so-called threshing tool for performing a threshing operation on the crop in order to separate the grain from the non-grain material such as straw. Typically, the straw is outputted by the harvester in such manner that it can be easily gathered into bales.

Because straw bales represent an important economic value, it is important to ensure that the process of gathering the straw is as efficient as possible, i.e. it is important to ensure that substantially all the straw that is outputted by the combine is gathered into bales. At present, the operator of the combine needs to check the quality of the straw as outputted manually and, based on its findings, adjust operational parameters of the threshing and separation tool. In order to maintain a desired quality of the straw, such a check should be done regularly at sufficiently small intervals to accommodate for varying crop conditions. This may however be rather time-consuming, resulting in an increased period of time for performing the harvesting process.

As such, there is a need to provide in an alternative way of assessing the quality of straw that is outputted by a combine.

SUMMARY OF THE INVENTION

It would be desirable to provide in an agricultural harvester which enables an assessment of the quality of straw in a more efficient manner. Therefore, the present invention provides, in an embodiment, in a monitoring system for a combine harvester, the monitoring system comprising:

a sensor configured to provide a measurement wave to a flow of crop residue on the harvester and to receive a response wave from the flow of crop residue;

a processor having an input terminal for receiving a response signal of the sensor representative of the response wave; the processor being configured to determine a crop parameter associated with the density of the flow of crop based on the response signal of the sensor;

the processor further comprising an output terminal for outputting a density signal representing the crop parameter.

The monitoring system according to the present invention, which may e.g. be mounted to a combine harvester for monitoring a flow of crop residue such as straw, enables to generate a signal, referred to as a density signal, representative of a crop parameter that can be associated with the density of the flow of crop residue. As an example, the crop parameter may e.g. be a height or thickness of the flow of crop residue, e.g. monitored as the crop residue progresses on the straw hood of the harvester, i.e. before being on the field.

In accordance with the present invention, the sensor is configured to provide a measurement wave to a flow of crop residue. Such a measurement wave may e.g. be an acoustic pulse, an ultrasonic pulse or an electromagnetic pulse or wave. In an embodiment, the sensor may e.g. include a transmitter configured to transmit the measurement wave, e.g. an acoustic or ultrasonic wave, to the flow of crop residue and a receiver configured to receive a response wave from the flow of crop residue.

In accordance with the present invention, the sensor may be applied in so-called reflective mode or transmissive mode. In the latter case, the response wave from the flow of crop material is the signal that remains after having passed through the flow of crop residue. In this case, the sensor may include a transmitter and a receiver that are arranged on opposite sides of the flow of crop residue. In the former case, the response wave may be a signal that is reflected off of the flow of crop residue. In this case, a transmitter and receiver of the sensor may be arranged on the same side of the flow of crop residue, e.g. adjacent to each other.

The monitoring system according to the present invention is configured to provide the measurement wave to the flow or crop residue, while the crop residue is on the harvester, e.g. being processed. This enables to provide in a more controlled monitoring of the crop residue parameters or quality compared to arrangements that sense a property of the crop residue when the crop residue is already outputted by the harvester and on the field. When the crop residue, e.g. straw in case of the harvesting of grain, is already outputted onto the field, an assessment of the density of the crop residue is more difficult and may e.g. required additional measurements such as ground level measurements or height or thickness measurements of the layer of crop residue on the field.

In an embodiment, the monitoring system is mounted to a combine harvester according to the present invention. In general, such an harvester comprises a header for harvesting a crop of a field, a threshing system for separating a crop residue from the harvested crop, and a monitoring system according to the invention. As an example, the harvester may be configured to harvest grain whereby the threshing system is configured to separate the grain and the straw, the straw thus being considered the crop residue. The use of the monitoring system according to the present invention on such a combine harvester enables to monitor the straw density prior to the straw being outputted onto the field, i.e. while the straw is still on the harvester, e.g. being processed or transported. As an example, the monitoring system may be configured to monitor the flow of straw while being transported on a so-called straw hood of the harvester. Such a straw hood may e.g. comprise a ramp that is mounted at a rear end of the harvester for guiding the flow of crop residue towards the field. The ramp may e.g. be a metal plate or the like.

In such embodiment, the sensor of the monitoring system may e.g. be mounted above the ramp such that the flow of crop residue passes in between the sensor and the ramp.

In an embodiment, the density signal is provided to an input terminal of a control unit of the harvester, the control unit being configured to control an operating parameter of the threshing system. In such embodiment, the control unit may further comprise a processor for processing the density signal and determining a control signal for the threshing system, in particular for controlling a component of the threshing system.

In general, it would be desirable to have the density of the layer of straw (also referred to as the swath) as low as possible, thus facilitating a subsequent pick-up of the straw for baling.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
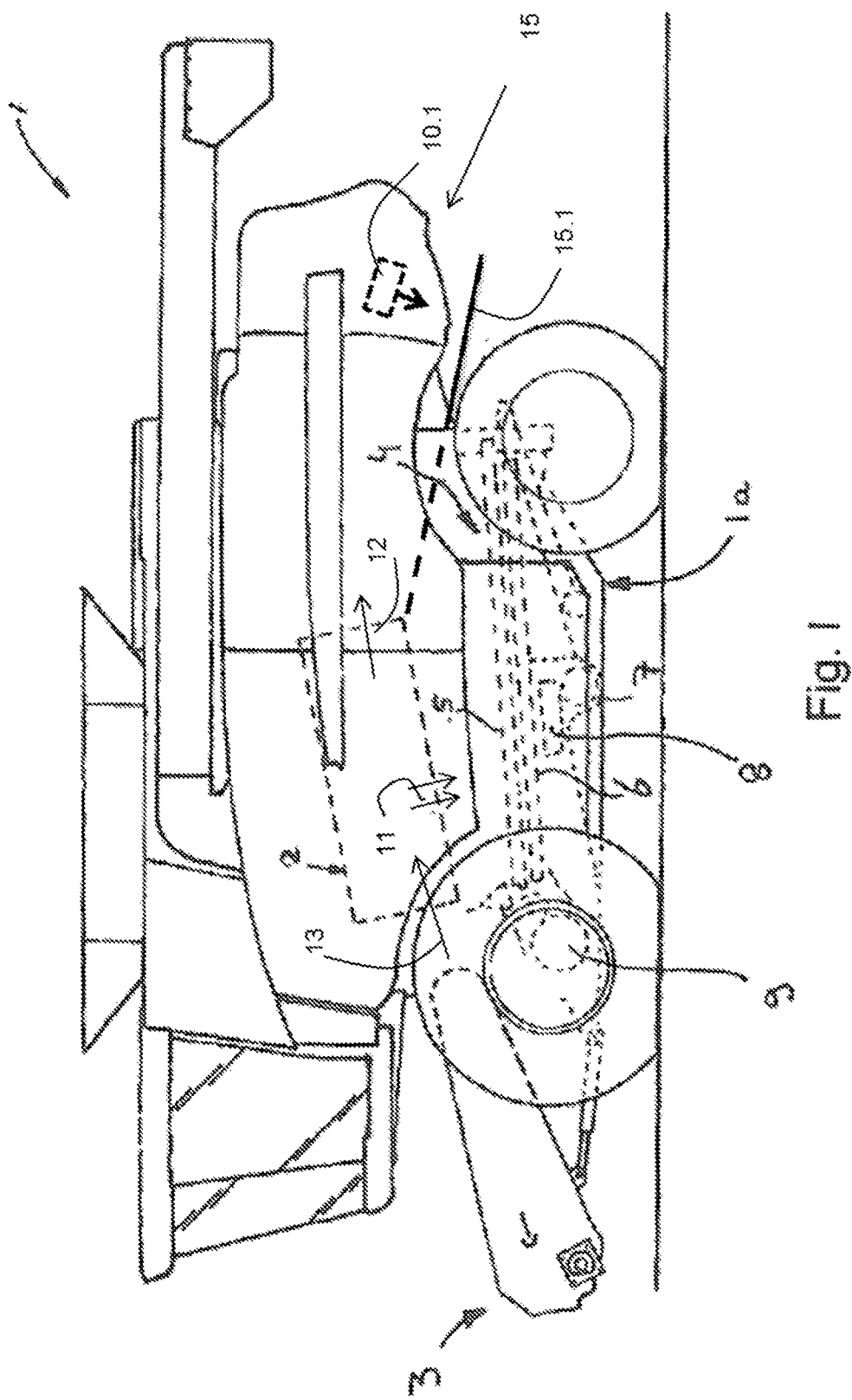
FIG. 1 depicts a monitoring system mounted to a combine harvester according to an embodiment of the present invention.

FIG. 1 depicts, in a cross-sectional view, a combine harvester 1 including a monitoring system 10 according to an embodiment of the present invention.

The agricultural harvester 1 can e.g. be configured to harvest grain as a crop, whereby straw can be considered a crop residue. In the harvester according to the present invention, this crop residue is monitored by a monitoring system configured to determine a signal that can be associated with the density of the crop residue, further on also referred to as a density signal. In the embodiment as shown, the monitoring system comprises a sensor 10.1. In case of the harvesting of grain, the crop residue, i.e. the straw may either be processed further and chopped into comparatively small parts that are left on the field, or it may be outputted onto the field and subsequently gathered into bales. In the latter case, it may be advantageous to ensure that the density of the straw as outputted onto the field is as low as possible, thereby facilitating the picking up of the straw. Without a monitoring system, the quality of the straw, i.e. reflected by the density, would have to be checked manually by the operator of the harvester. In such case, this check would have to be repeated regularly, in order to take varying harvesting conditions into account. Such a repeated check may however be time-consuming and adversely affects the harvesting time required. By substantially continuously monitoring the density of the straw, e.g. using a monitoring system according to the present invention, a more effective subsequent baling of the straw can be realized.

Further, the monitoring system according to the present invention is configured to monitor the flow of crop residue while on the harvester. This provides in a more controlled environment to monitor the crop residue compared to the use of monitoring system that monitors the swath of straw on the field. In the latter case, estimating the density of the swath may be cumbersome and may involve determine the height of the swath and a ground level.

By sensing the crop residue on the harvester, rather than on the field, a more accurate determination of the density may be obtained. In addition, in case the density signal is applied in a control loop of the threshing system of the harvester (see further on), a faster response may be realized compared to a sensing of the crop residue density on the field.

The agricultural harvester 1 as schematically shown in FIG. 1 further comprises a header 3 or harvesting mechanism for cutting a crop on a field. The cup crop is subsequently transported, e.g. by means of one or more augers or one or more conveyers to a threshing mechanism or threshing system 2 configured to separate the cut crop into a first stream or flow (indicated by the arrow 11), substantially composed of grain and chaff, and a second stream or flow (indicated by the arrow 12), referred to as the crop residue, substantially composed of straw.

Figure 3:
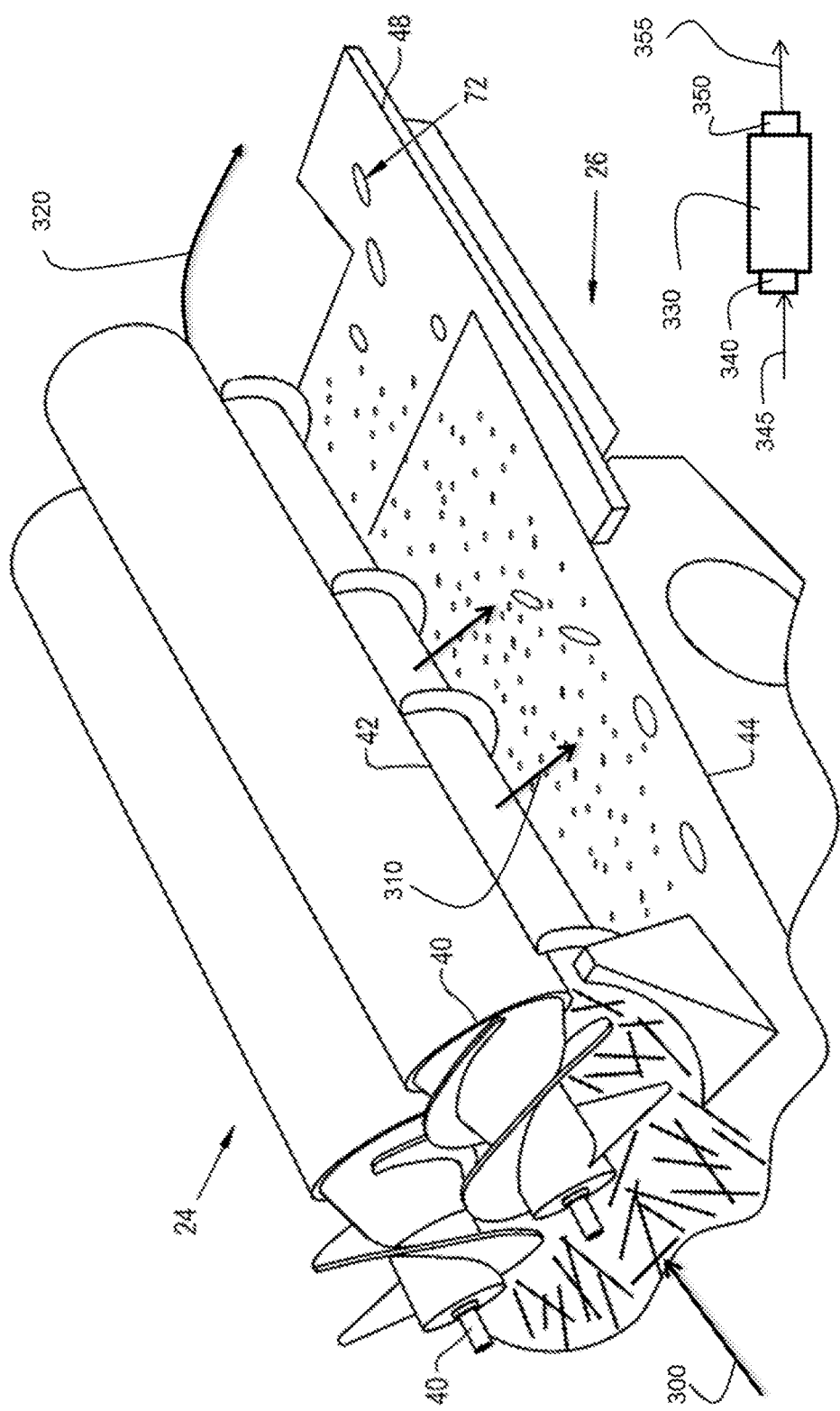
FIG. 3 depicts a threshing and separation system as can be applied in a combine harvester according to the present invention.

In an embodiment, as shown in more detail in FIG. 3, the threshing system 2 is of an axial flow type including a rotor that is at least partially enclosed by and rotatable within a corresponding perforated concave. The cut crop that enters the threshing system 2 (indicated by arrow 13) is threshed and separated by the rotation of the rotor within the perforated concave, thereby providing the separation into the first stream or flow (through the perforations of the perforated concave) and the second stream that exits the threshing system in axial direction. The first stream 11 may e.g. be conveyed via a grain pan to a cleaning mechanism 4, e.g. including one or more sieves 5, 6, driven by a drive assembly 8. The fine material, e.g. grain, that is collected below the sieves is transported by means of an auger 7, e.g. to an elevator. The second stream 12 is conveyed to an outlet of the harvester, e.g. comprising a straw hood 15. In the embodiment as shown, the straw hood 15 comprises a ramp 15.1 via which the a flow of crop residue, e.g. straw, can be outputted onto the field.

In the embodiment as shown, the harvester further includes a monitoring system including a sensor 10.1, the sensor being configured to provide a measurement wave to the flow of crop residue on the harvester, in particular on the ramp 15.1, and to receive a response wave from the flow of crop residue. In order to realize this, the sensor 10.1 is, in the embodiment as shown, mounted substantially above the ramp 15.1. In the arrangement as shown, the sensor may e.g. include a transmitter for transmitting an ultrasonic signal, e.g. an ultrasonic pulse towards the ramp 15.1. In case there is no straw being outputted, a return pulse will be received, e.g. by a receiver of the sensor 15.1 at a particular instance, depending on the distance between the sensor and the ramp. In case straw is present on the ramp (see FIG. 2a), a multiple return pulses may be received.

Figure 2A:
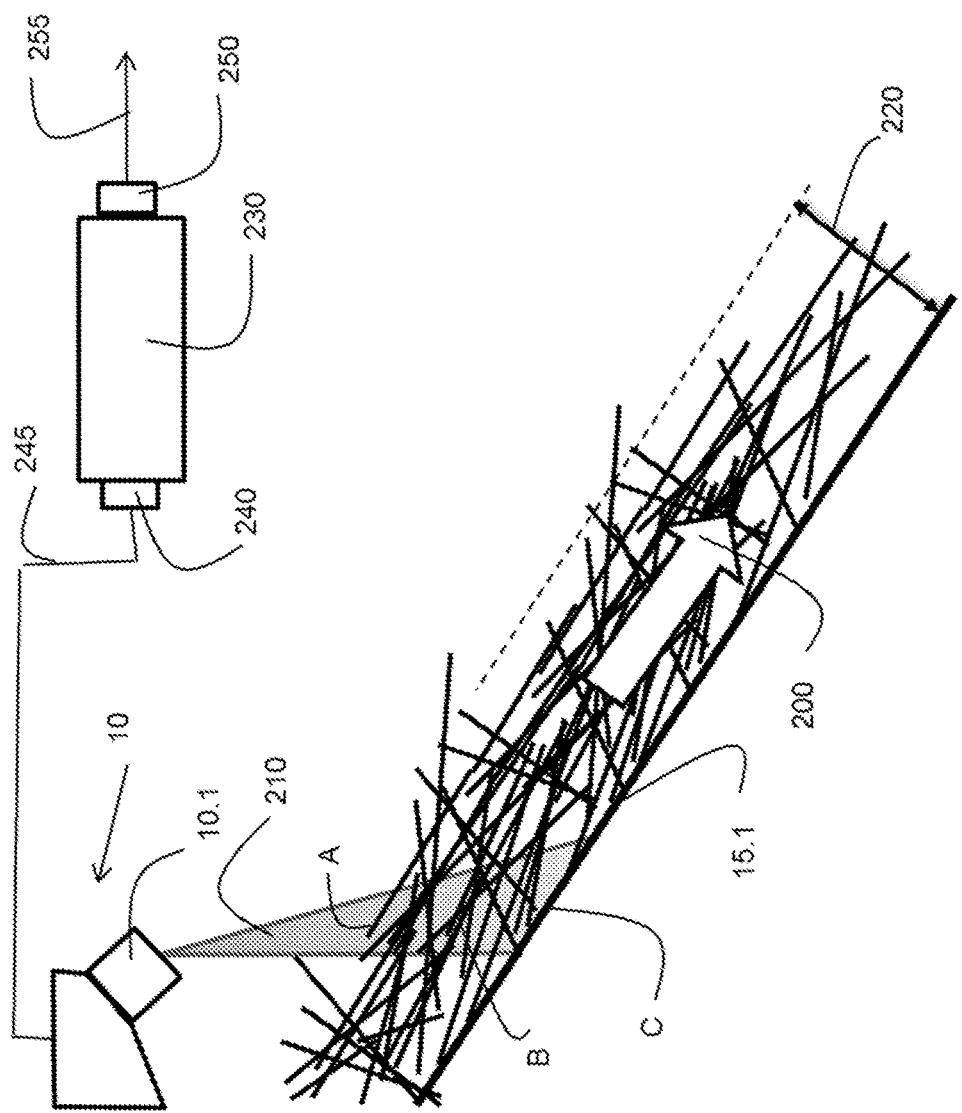
FIG. 2a depicts a monitoring system according to an embodiment of the present invention.

FIG. 2a schematically shows in more detail an embodiment of the monitoring system 10 according to the present invention.

FIG. 2a schematically shows a flow (indicated by the arrow 200) of straw that is outputted onto a field via a ramp 15.1 of a straw hood of a combine harvester. FIG. 2a further shows a monitoring system 10 configured to monitor the flow of crop residue 200 on the harvester, i.e. on the ramp 15.1 of the harvester. The monitoring system 10 as shown comprises a sensor 10.1 configure to send a measurement wave 210 to the flow of crop residue 200 on the ramp 15.1. in the embodiment as shown, the wave 210 may be an ultrasonic pulse that is projected towards the ramp 15.1. Due to the presence of the flow of crop residue, the ultrasonic pulse can be reflected at various positions on and in the layer of crop residue, resulting in multiple reflections that may be received by a receiver of the sensor 10.1.

In an embodiment, the sensor 10.1 may thus comprises a transmitter for transmitting a signal such as an ultrasonic pulse 210 to the flow of crop residue on the harvester and a receiver for receiving a return signal. In such embodiment, the transmitter and receiver may be arranged adjacent to each or may be somewhat separated from each other. As will be understood by the skilled person, the angle at which the pulse 210 impacts the ramp 15.1 may affect the direction of the reflected pulse or pulses and may thus have an effect on the appropriate or most effective location for positioning the receiver of the sensor. In an embodiment, the sensor is configured to send the pulse to the straw hood, i.e. to the ramp 15.1 of the straw hood in a direction substantially perpendicular to a plane of the straw hood. In such embodiment, it may be advantageous to locate the receiver close to the transmitter.

In an embodiment, the functionality of a transmitter and a receiver may be combined in a so-called transceiver which may both be configured to transmit a pulse an pick or receive any reflected pulses in response to the transmitted pulse.

Figure 2B:
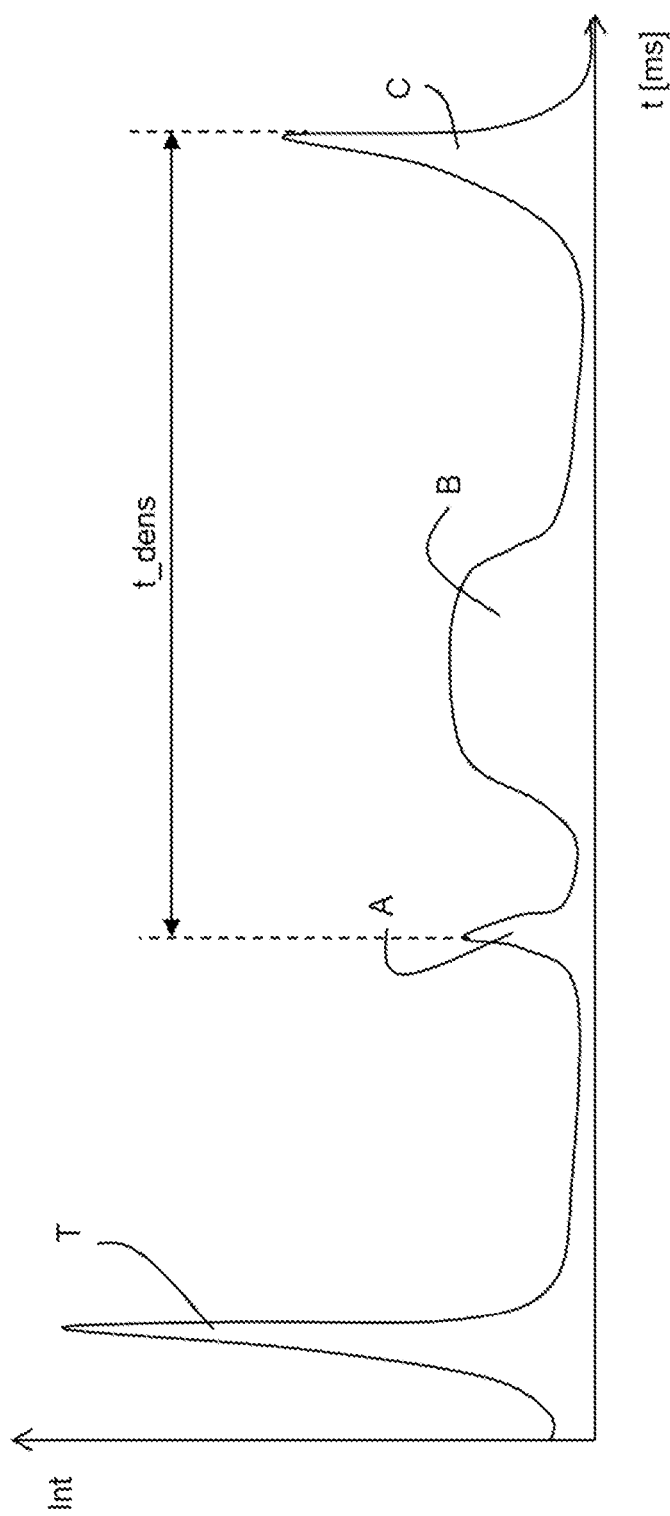
FIG. 2b depicts an applied pulse and response pulses using a monitoring system according to the present invention.

FIG. 2b schematically depicts an intensity level Int of a transmitted pulse T and a subsequent response comprising reflected pulses A, B, and C. in FIG. 2a, the locations A, B, and C are used to indicate the positions from which the respective reflected pulses originate.

Depending on the size and structure of the flow of crop residue, e.g. straw, multiple reflected pulses may be observed, e.g. by a receiver of the sensor 10.1. Since reflected pulse A is the first pulse to be received by the receiver, one can assume the location from which reflected pulse A originates to be the closest to the receiver of the sensor. As such, reflected pulse A can be assumed to originate from the top surface of the layer of crop residue, as indicated in FIG. 2a. As can be seen in the intensity level graph of FIG. 2b, reflected pulse C is the last pulse to be received by the receiver. As such, it can be assumed that this pulse represents a reflection on the straw hood itself, i.e. on the ramp 15.1 of the straw hood.

As such, the time or period t_dens indicated in FIG. 2b, i.e. between the receipt of the first reflected pulse A and the last reflected pulse C can be considered a value that is proportional to the thickness of the flow of crop residue 200, the thickness of the layer being indicated by reference number 220 in FIG. 2a. Further, one or more intermediate reflected pulses, such as pulse B may be present as well.

In accordance with the present invention, the monitoring system 10 further comprises a processing unit 230 having an input terminal 240 to receive a response signal 245 of the sensor 10.1 representative of the response wave, e.g. the reflected pulses as shown in FIG. 2b. Such a processing unit can be embodied as a processor, a microprocessor, a computer or the like and in general comprises a memory unit for storing data such as the response signal and a computational unit for processing the data. In accordance with the present invention, the processor 230 is configured to determine a crop parameter associated with the density of the flow of crop based on the response signal of the sensor. In the example given in FIG. 2a, the height or thickness 220 of the flow of crop residue can be considered such a crop parameter. As indicated, this parameter may be derived based on the assessment of the timing of the received pulse or pulses. In accordance with the present invention, the processor 230 further comprises an output terminal 250 for outputting a density signal 255 representing the crop parameter. Such a density signal 255 may e.g. be provided to a control unit of to combine harvester to which the monitoring system is mounted, e.g. to control a threshing system of the harvester.

With respect to the sensor arrangement as schematically shown in FIG. 2a, it can be noted that the arrangement of transmitter and receiver as displayed operates in a reflective mode; i.e. the receiver of the sensor being arranged to receive a reflected pulse or pulses. It should however be noted that sensor arrangements that operate in a transmissive mode can be considered as well. In such arrangement, the receiver may e.g. be mounted in such manner that the flow of crop residue is between the transmitter and the receiver. Referring to FIG. 2a, such an arrangement may be obtained by mounting the receiver onto the ramp 15.1.

In such embodiment, the intensity of the wave as received by the receiver compared to the wave that was emitted by the transmitter, can be considered an indication of the density of the crop residue. More specifically, in case the density of the crop residue is comparatively low, the intensity of the wave as received by the receiver on the ramp 15.1 may be comparatively high and vice versa.

In an embodiment, the monitoring system according to the present invention provides in a more detailed density signal, by taking additional parameters into account.

In an embodiment, the processing system may be configured to receive, as an input, a value of the width of the flow of crop residue, e.g. corresponding to the width of the straw hood or ramp 15.1 of the straw hood. Note that a value of the width may e.g. be derived from an operating parameter or setting of the straw hood or may be derived from a measurement. In particular, a similar measurement as described with respect to determining the height of the flow of crop residue may be applied to determine the width of the flow of crop residue.

In an embodiment, the monitoring system is further provided with a velocity sensor configured to provide a velocity signal representative of the velocity of the flow of crop residue. Such a velocity sensor may e.g. be an image based sensor configured to capture one or more images of the crop residue passing at a particular position and provide the images to the processing unit of the monitoring system. Using pattern recognition (or pixel flow or other image processing techniques like cross-correlation of 2 or more images obtained after each other in time . . . ), the processing unit may process the images to derive a velocity of the flow of crop residue.

Combined with information on the height and the width of the flow of crop residue, the velocity signal enables the processing unit to derive an estimate of the volume of crop residue that is outputted per unit of time.

In an embodiment, the monitoring system may further include a sensor for assessing the infeed of the harvester, i.e. the amount of crop that is being harvested, i.e. taken in by the header of the harvester. Such sensors may e.g. be image based sensors or laser based sensors or even radar based sensors. Based on input signals from such sensors, the processing unit of the monitoring system according to the present invention may e.g. determine or estimate the weight of crop residue that is processed per unit of time. Combined with volume of crop residue that is outputted per unit of time, the density of the crop residue may e.g. be determined or estimated.

In an embodiment, as explained in more detail below, the density signal as determined by the monitoring system according to the present invention may be applied in a combine harvester according to the present invention to control an operating parameter of the threshing system of the harvester. In such embodiment, the harvester may e.g. comprise a control unit for controlling an operating parameter of the threshing system, the control unit comprising:

an input terminal for receiving the density signal;

a processor for processing the density signal and determining a control signal for the threshing system based on the density signal; and an output terminal for outputting the control signal to the threshing system to control the operating parameter.

In an embodiment, the functionality of the processing unit of the monitoring system and the control unit of the harvester may be combined and integrated in a single control unit or controller.

FIG. 3 schematically shows an example of a threshing system 24 as can be applied in an harvester according to the present invention. The threshing system 24 as shown includes a rotor 40 that is at least partly surrounded by a perforated concave 42. By the rotation of the rotor 40, the cut or harvested crop 300 is threshed and separated into a flow of larger elements 310 such as stalks or straw and a flow of smaller elements 320 including grain 72 and smaller non-grain material such as chaff and dust. The latter flow may e.g. be processed by a cleaning system 26 that includes sieves a grain pan 44 and sieves 46 and 48.

In accordance with an embodiment of the present invention, the operation of the threshing system 24 can be controlled by a control unit 330 having an input terminal 340 and an output terminal 350, the input terminal being configured to receive the density signal 345, e.g. density signal 245 as shown in FIG. 2a, from the processing unit of the monitoring system.

The control unit 330 is configured to determine, based on the density signal, a control signal 355 (outputted via the output terminal 350) for controlling an operation of the threshing system 24. As an example, based on the density signal, the control unit may e.g. determine that the velocity of the rotor 40 should be adjusted or that a spacing between the rotor 40 and the perforated concave 42 should be adjusted, in order to obtain a more preferred density of the flow 320 of crop residue, i.e. a reduced density.

In an embodiment, the density signal as applied to the control unit 330 may be obtained by processing any of the further parameters or measurements as described above, i.e. the width of the flow of crop density or the velocity of the flow of crop density or a signal representing the infeed or intake of the harvester.

In an embodiment, the control unit may further be configured to receive, as an input signal, a power signal representative of the power consumption of the threshing system. It has been observed that the power consumption of the threshing system can be an indication of the size or average size of the flow or straw, i.e. crop residue, that is outputted by the threshing system. Further, the smaller the size or average size of the crop residue, the higher the density of the crop residue. As such, a signal representing the power consumption of the threshing system may be applied, by the control unit, as an indication of the straw quality, in particular the straw density. As such, in an embodiment of the present invention, the control unit of the combine harvester may be configured to determine a control signal for controlling an operation or operational parameter of the threshing system based on both the density signal as received from the monitoring system and the power signal (e.g. obtained from a power sensor associated with the threshing system).

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

A single processor or control unit may fulfil the functions of several items recited in the claims.

The invention claimed is:

1. A monitoring system for a combine harvester, the monitoring system comprising:
a sensor configured to provide a measurement wave to a flow of crop residue that is outputted onto a field via a ramp of a straw hood of the harvester and to receive a response wave from the flow of crop residue; and
a processor comprising an input terminal for receiving a response signal of the sensor representative of the response wave, the processor configured to determine a crop parameter associated with a density of the flow of crop residue based on the response signal of the sensor, the crop parameter comprising a layer thickness of the flow of crop residue as the crop residue progresses on the ramp of the straw hood of the harvester, the processor further comprising an output terminal for outputting a density signal representing the crop parameter.

2. The monitoring system according to claim 1, wherein the sensor is an ultrasonic sensor including a transmitter configured to transmit the measurement wave to the flow of crop residue and a receiver configured to receive the response wave from the flow of crop residue.

3. The monitoring system according to claim 2, wherein the transmitter is configured to output an ultrasonic pulse as the measurement wave, the receiver being configured to receive, as the response wave, a response of the ultrasonic pulse after impacting the flow of crop residue.

4. The monitoring system according to claim 2, wherein the transmitter and receiver are configured in a transmissive operating mode or a reflective operating mode.

5. The monitoring system according to claim 1, further comprising a velocity sensor configured to generate a velocity signal representing a velocity of the flow of crop residue.

6. The monitoring system according to claim 1, wherein the processor is further configured to receive an operating parameter of the combine harvester and determine a volume of the flow of crop residue based on the operating parameter of the harvester and the response signal.

7. The monitoring system according to claim 1, wherein the processor is further configured to receive an intake parameter representing a weight per unit of time of the flow of crop residue.

8. The monitoring system according to claim 1, wherein the crop residue comprises straw.

9. A combine harvester comprising:

a header for harvesting a crop of a field;

a threshing system for separating a crop residue from the harvested crop;

a straw hood including a ramp for guiding a flow of crop residue towards the field; and a monitoring system, including:

a sensor configured to provide a measurement wave to the flow of crop residue that is outputted onto the field via the ramp and to receive a response wave from the flow of crop residue, the sensor mounted within the harvester above the ramp such that, during use, the flow of crop residue is arranged between the sensor and the ramp; and a processor having an input terminal for receiving a response signal of the sensor representative of the response wave, the processor configured to determine a crop parameter associated with a density of the flow of crop residue based on the response signal of the sensor, the crop parameter comprising a layer thickness of the flow of crop residue as the crop residue progresses on the ramp of the straw hood of the harvester, the processor further comprising an output terminal for outputting a density signal representing the crop parameter.

10. The combine harvester according to claim 9, further comprising a control unit for controlling an operating parameter of the threshing system, the control unit comprising:

a second input terminal for receiving the density signal;

a second processor for processing the density signal and determining a control signal for the threshing system based on the density signal; and a second output terminal for outputting the control signal to the threshing system to control the operating parameter.

11. The combine harvester according to claim 10, wherein the threshing system comprises a rotor that is at least partially enclosed by a perforated concave, the operating parameter being a position of the concave relative to the rotor or a velocity of the rotor.

* * * * *